United States Patent
Hieshima et al.

(10) Patent No.: US 6,361,558 B1
(45) Date of Patent: *Mar. 26, 2002

(54) STENT ANEURYSM TREATMENT SYSTEM AND METHOD

(75) Inventors: Grant Hieshima, Huntington Beach, CA (US); Donald K. Jones, Lauderhill; Vladimir Mitelberg, Miami, both of FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,318

(22) Filed: May 9, 2000

Related U.S. Application Data

(62) Division of application No. 09/052,402, filed on Mar. 31, 1998, now Pat. No. 6,063,111.

(51) Int. Cl.⁷ .................................................. A61F 2/06
(52) U.S. Cl. ........................ 623/1.16; 623/11; 623/12; 623/1.1; 606/191
(58) Field of Search .................... 606/1, 108, 159, 606/191–200; 604/507; 623/1, 11, 12, 1.1, 1.11, 1.16, 1.2, 1.22, 1.35; 128/898

(56) References Cited

U.S. PATENT DOCUMENTS

| | | | |
|---|---|---|---|
| 3,868,956 A | | 3/1975 | Alfidi et al. |
| 4,512,338 A | * | 4/1985 | Balko et al. .................. 128/1 |
| 4,560,374 A | | 12/1985 | Hammerslag |
| 4,580,568 A | | 4/1986 | Gianturco |
| 4,733,665 A | | 3/1988 | Palmaz |
| 4,739,762 A | | 4/1988 | Palmaz |
| 4,776,337 A | | 10/1988 | Palmaz |
| 5,102,417 A | | 4/1992 | Palmaz |
| 5,609,625 A | | 3/1997 | Piplani et al. |
| 5,980,514 A | * | 11/1999 | Kupiecki et al. ............. 606/32 |
| 6,063,111 A | * | 5/2000 | Hieshima et al. ............. 623/1 |

FOREIGN PATENT DOCUMENTS

| | | | | |
|---|---|---|---|---|
| FR | 2 678 508 | * | 1/1993 | ................. 623/1 |
| IT | WO 96/41592 | * | 12/1996 | ................. 623/1 |

\* cited by examiner

Primary Examiner—Glenn K. Dawson
Assistant Examiner—Jennifer Maynard
(74) Attorney, Agent, or Firm—Henry W. Collins

(57) ABSTRACT

A vascular stent for opening blood vessel occlusions and for providing support to damaged areas of blood vessel sites includes a proximal end defining a first lumen opening. The helical stent is constructed from a resilient material and has a body portion extending from the proximal end to define a lumen. A distal end defines a second lumen opening a predetermined axial distance from the first lumen opening. The stent is maintained in a stretched linear state when in a catheter for delivery to a vascular site, and resiliently expands into a relaxed helical shape when released from the catheter. Various embodiments of the present invention are disclosed, including a stent made of a wire having a flattened cross-section, a helical wire stent having a flat ribbon to span between adjacent loops of wire, multiple intertwined stents in the same blood vessel. A preferred embodiment of the present invention involves treating an aneurysm formed at a vessel branching by arranging multiple helical wire stents in each vessel.

5 Claims, 5 Drawing Sheets

STENT ANEURYSM TREATMENT SYSTEM AND METHOD

This appln is a Div. of Ser. No. 09/052,402 filed Mar. 31, 1998, U.S. Pat. No. 6,063,111.

BACKGROUND AND SUMMARY OF THE INVENTION

1. Technical Background

The present invention relates generally to treating vascular defects, and more particularly, to a stent system and method for repair and treatment of blood vessels.

2. Discussion

On a worldwide basis, nearly one million balloon angioplasties were performed in 1997 to treat vascular disease, including blood vessels clogged or narrowed by a lesion or stenosis. The objective of this procedure is to increase the inner diameter or cross-sectional area of the vessel passage, or lumen, through which blood flows. Unfortunately, the lumen often closes or narrows again within six months after balloon angioplasty, a phenomenon called restenosis.

Another serious vascular defect is an area of weakened vessel wall that causes a bulge or bubble to protrude out in a radial direction from the adjacent vessel. This type of defect is called an aneurysm. If untreated, the aneurysm may continue expanding until it bursts, causing hemorrhage.

In an effort to prevent restenosis or treat an aneurysm without requiring surgery, short flexible cylinders or scaffolds made of metal or polymers are often placed into a vessel to maintain or improve blood flow. Referred to as stents, various types of these devices are widely used for reinforcing diseased blood vessels, for opening occluded blood vessels, and for defining an internal lumen bulkhead to relieve pressure in an aneurysm. The stents allow blood to flow through the vessels at an improved rate while providing the desired lumen opening or structural integrity lost by the damaged vessels. Some stents are expanded to the proper size by inflating a balloon catheter, referred to as "balloon expandable" stents, while others are designed to elastically resist compression in a "self-expanding" manner.

Balloon expandable stents and self-expanding stents are generally delivered in a cylindrical form, crimped to a smaller diameter around some type of catheter-based delivery system. When positioned at a desired site within the lesion, they are expanded by a balloon or allowed to "self-expand" to the desired diameter. However, many vessels are too small to accept a stent shaped in a cylinder during delivery.

Another type of stent is formed of a wire that has a relaxed cylindrical shape, yet can be stretched into a linear shape for delivery through a much smaller catheter than any stent delivered in cylindrical form. The basic design of such a "linear" stent is described in U.S. Pat. No. 4,512,338, issued Apr. 23, 1985 to Balko, and is of course acceptable for certain applications.

Balko discloses a shape memory nitinol wire, shaped in its parent phase into a coil of adjacent wire loops, then cooled to its martensite phase and reshaped to a straight shape. The wire is inserted into the vessel with thermal insulation, such that the wire reforms to its coil shape upon the removal of the insulation means, so as to reform the damaged vessel lumen.

However, this basic linear stent often creates gaps between adjacent helical portions of wire in its deployed shape, gaps which may thrombose or restenose. Moreover, many aneurysms form at a bifurcation, where one vessel branches off from another, but the basic linear stent is generally ineffective treatment for such a bifurcation aneurysm.

As a result, there is a need for an improved stent that can be easily delivered to a vascular site through a very small catheter, that is capable of being atraumatically repositioned, and that exhibits sufficient structural integrity and resilience under inward forces. It is also desirable that this improved stent be designed to reduce the possibility of interstitial gaps, and it is preferable that the stent system be capable of effectively treating a bifurcation aneurysm.

The present invention provides an intravascular stent constructed from a resilient or superelastic material for holding open an occluded vessel passageway, or for providing support to a damaged vessel site such as an aneurysm. Preferably, the stent of the present invention can be delivered in a linear fashion through a small catheter, yet can expand into a relaxed cylindrical shape on deployment from the catheter. Moreover, the stent system of the present invention can effectively treating a bifurcation aneurysm, by providing a pair of meshed stents extending into the branches of a bifurcation, thus building a "shelf" for supporting embolic devices or materials in the aneurysm.

The stent is substantially helical in its relaxed state, formed of a spiral wire having a pitch of preferably about 0.125 inches. Its helical shape defines a passageway or lumen, and is inserted into the vessel near the damaged or occluded vessel site through a catheter smaller in diameter than the deployed stent itself. The stent can be stretched to a substantially linear shape for insertion within the lumen of a catheter. When released from the catheter into the vessel, the stent tends to assume a helical configuration, thereby expanding in diameter and maintaining its position at the vessel site, where it exerts a radially outward force tending to hold open the vessel.

In particular, the stent of the present invention exhibits a relaxed helical configuration that includes a proximal end defining a first stent passageway opening. A body portion extends from the proximal end and defines a passageway. A distal end of the stent terminates the body portion and defines a second passageway opening a predetermined axial distance from the first passageway opening.

These and various other objects, advantages and features of the invention will become apparent from the following description and claims, when considered in conjunction with the appended drawings.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
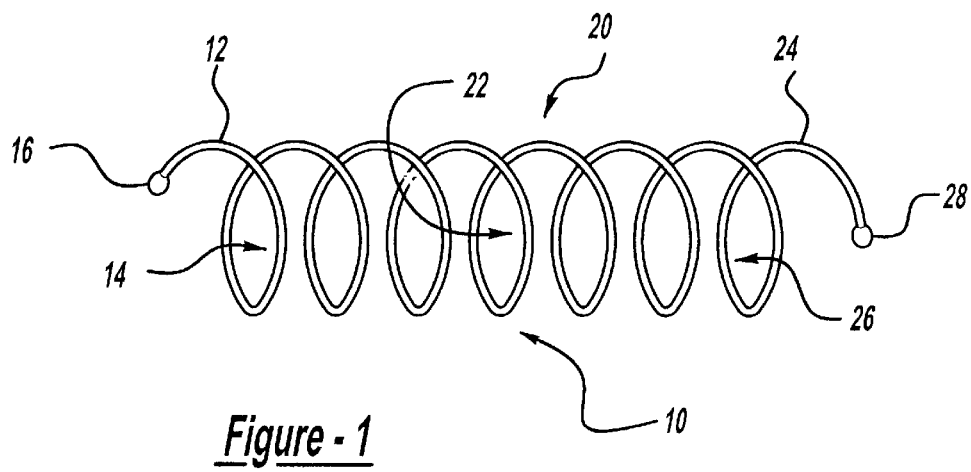
FIG. 1 is a perspective view of an intravascular stent formed according to a preferred embodiment of the present invention in a helical configuration in its relaxed state.
Figure 1A:
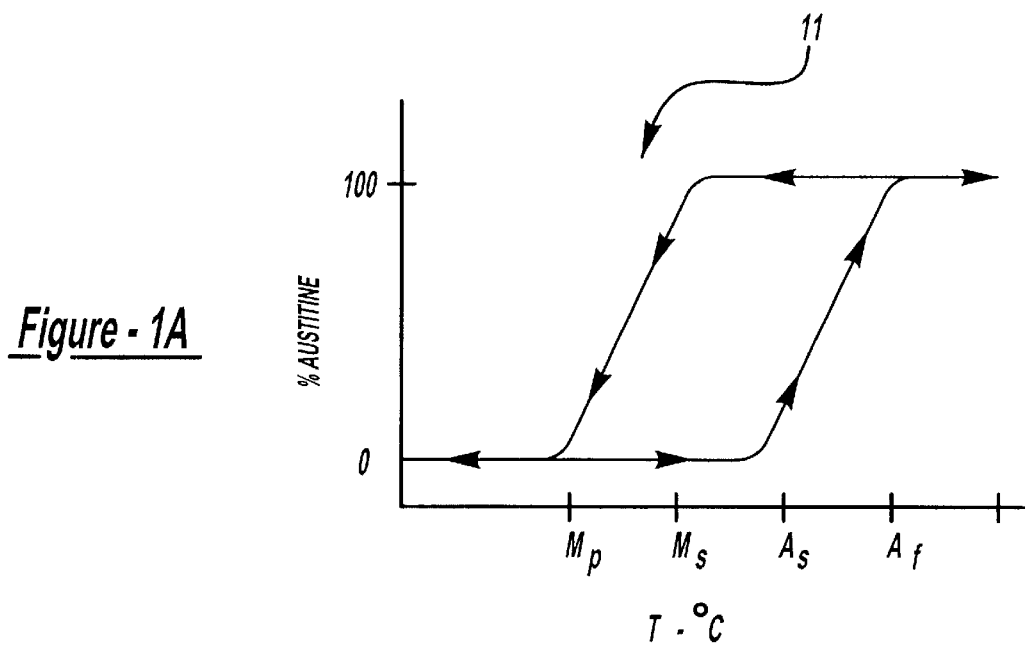
FIG. 1A graphically illustrates the possible phase changes of the stent of the present invention in both a deployed and non-deployed state.

Referring to FIG. 1, a perspective view of a stent according to a first preferred embodiment of the present invention is shown generally at 10. The stent 10 may be used to reinforce diseased areas of a blood vessel, such as aneurysms, and for opening narrowed blood vessels to increase blood flow. The stent 10 is preferably formed from a single length of nickel-titanium alloy wire, which is available under the name of nitinol, or from any other suitable resilient material. The nitinol wire preferably has an austenitic phase transformation substantially below 37° C., as is shown at reference numeral 11 in FIG. 1A, thus giving the stent a relaxed resilient state at body temperature. The phase transformation behavior illustrated in FIG. 1A is inherent to the nitinol material, and can be used for "shape memory" material applications. The present stent requires no shape memory attributes, and preferably remains in the resilient, or "super-elastic" phase.

Preferably, the nitinol wire is wound around a piece of threaded titanium in a helical configuration and heat-treated to form the stent in a relaxed state helical configuration as shown in FIG. 1. Further, all or part of the wire material may be coated or covered with a radiopaque material, such as a platinum coating or very small platinum coil. This radiopaque material allows visualization of the stent while in the body of the patient, during insertion and after placement of the stent at the vessel site.

Figure 1B:
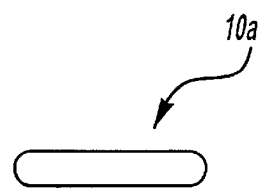
FIGS. 1B and 1C illustrate alternate cross-sections of the stent wire material.
Figure 1C:
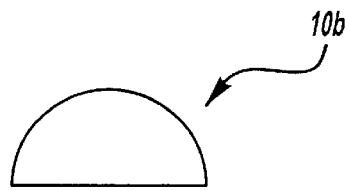

The stent 10 preferably has a deployed diameter of approximately 0.039–0.393 inches, and has a deployment length of approximately 0.125–2.00 inches. However, the stent diameter and length may vary in size depending upon the particular application and the size of the blood vessel in which the stent is to be inserted. As shown in FIGS. 1B and 1C, the stent may have a substantially flat cross-section as shown at 10a, or a semi-circular or "D" shaped cross-section as shown at 10b, or any other cross-section as dictated by a particular application or anatomy.

The stent 10 of the present invention includes a proximal end 12 defining a stent passageway opening 14. The stent proximal end 12 may include a beaded tip 16 that provides a point at which a stent delivery device, such as the pusher mechanism shown at 18 in FIG. 3, may be attached or engaged with the stent, to advance the stent through the vessel to the diseased vessel site. The pusher mechanism 18 may be capable of selective engagement with the stent proximal bead 16, so that the pusher mechanism 18 can selectively release the stent at whatever location is desired. As a result, the stent can be more precisely placed before being released by the pusher mechanism 18, or may even be retracted back into the catheter if the stent is the wrong size or is positioned improperly.

The stent also includes a body portion 20 extending from the proximal end in a helical configuration. The body portion 20 defines a stent lumen 22 that allows passage of blood or other bodily fluids. Preferably, the helical configuration of the body portion has a characteristic pitch of approximately 0.003–0.250 inches, with the term "pitch" being defined as the center to center axial distance between adjacent coils in the helical configuration.

The stent also includes a distal end 24 which terminates the body portion 20 and which defines a second lumen opening 26 for the stent lumen 22. The distal end terminates at a distal tip 28, which may preferably have a bead to be atraumatic to the blood vessel into which the stent is inserted.

Figure 2:
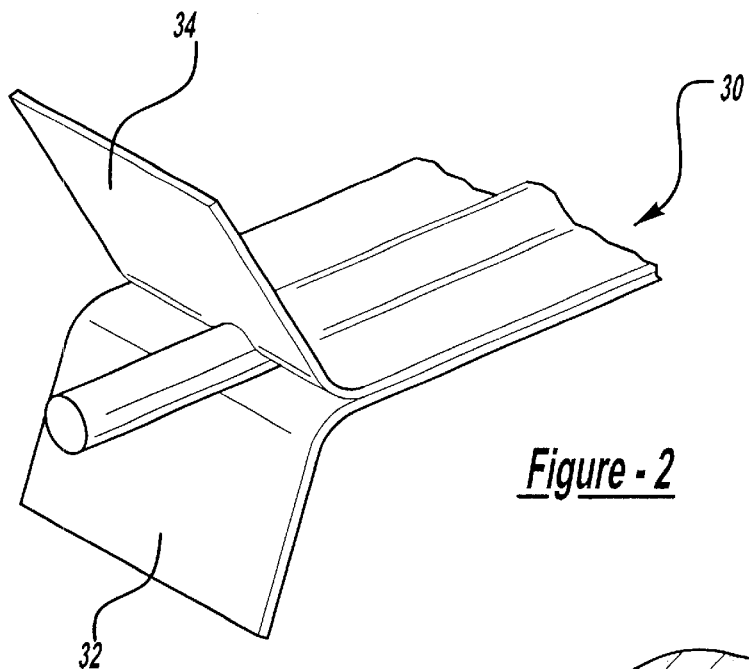
FIG. 2 is an enlarged view of a portion of a stent according to a second preferred embodiment of the present invention.
Figure 2A:
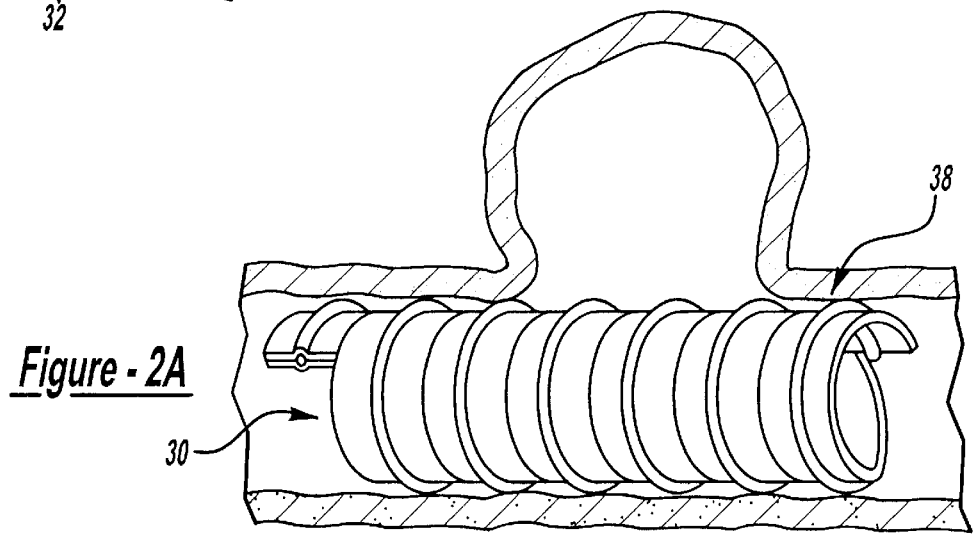
FIG. 2A illustrates the stent of FIG. 2 in a deployed state.

Referring to FIG. 2, an enlarged section of a stent according to a second preferred embodiment of the present invention is shown generally at 30. The resilient wire of the stent is sealed between two sheets or strips of film or mesh 32 and 34, defining a first and second flap extending outward from the wire. The outer strip of film 32 may be a thrombogenic film to aid in securing the stent to the wall of the vessel in which the stent is implemented. In contrast, the inner strip of film 34 is preferably a non-thrombogenic film material to prevent thrombus within the stent lumen, so as not to inhibit blood flow. As shown in FIG. 2A, after the stent exits the microcatheter, it forms a helical configuration with the edges of the attached films 32 and 34 overlapping, to form a tubular structure 38. The thrombogenic side of the film 32 is on the outside of the tubular structure 38, and the non-thrombogenic side of the film 34 is on the inside of the tubular structure 38.

Figure 3:
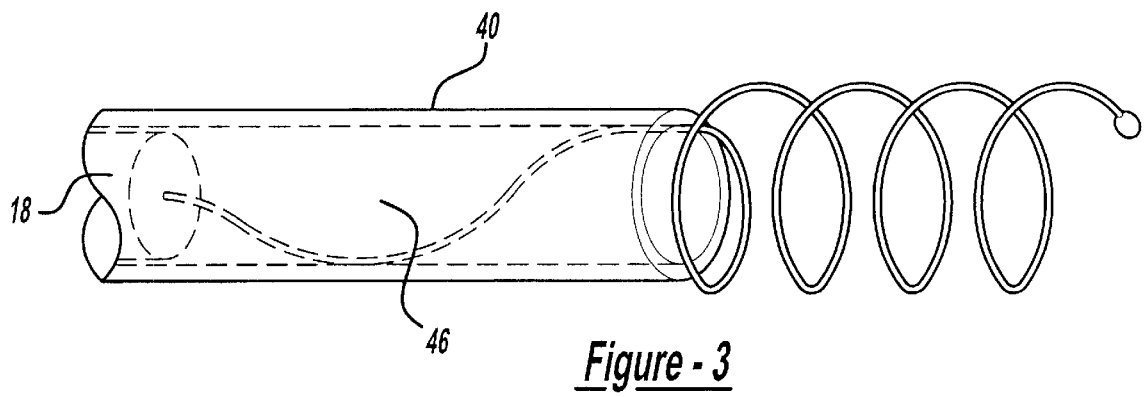
FIG. 3 is a side elevation view of the stent of FIG. 1 inserted into a microinfusion catheter for intravascular placement according to the preferred embodiment of the present invention.
Figure 4:
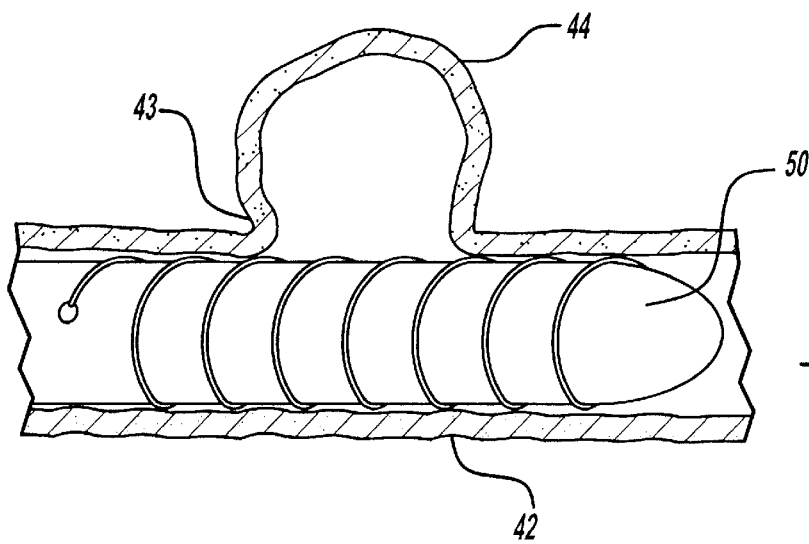
FIG. 4 illustrates the stent of FIG. 3 fully deployed in a blood vessel adjacent an aneurysm, in addition to a balloon inflated within the stent.

Referring to FIGS. 3 and 4, the stent 10 is shown after being inserted into a microcatheter 40 for deployment in a weakened or occluded area of a vessel 42, such as a neck 43 of an aneurysm shown at 44. The stent 10 is pushed through the microcatheter 40 by an operator manipulating the delivery device or pusher mechanism 18. The microcatheter 40 is of a type well known in the art and has a diameter smaller than that of the stent in its deployed configuration. For example, for a stent having a non-deployed or stretched linear wire diameter of 0.016 inches, the microcatheter used to deploy the stent would preferably have an inside diameter of about 0.020 inches, while the deployed diameter of the coiled stent could be much larger, perhaps as much as 0.157 inches.

The microcatheter 40 delivers the stent in a substantially linear configuration while being delivered through the microcatheter, and releases the stent to its substantially helical configuration upon exiting the microcatheter 40.

In the initial linear configuration, the stent can be delivered to a vessel location through a catheter having a diameter significantly smaller than that of the relaxed, deployed stent. The stent of the present invention thereby minimizes the diameter of the catheter in the vessel, and thereby facilitates deployment of a stent in small diameter vessels not currently treatable with tubular or cylindrical stents having the same deployed diameter.

As shown in FIG. 4, after being deployed in the vessel area, the stent returns to its relaxed helical configuration, thereby expanding to its normal diameter and tending to retain itself in position within the smaller diameter blood vessel 42. Further, as shown in FIG. 4, a balloon 50 of the type associated with conventional balloon microcatheters may also be utilized to aid in expanding or "tacking" the stent of the present invention.

Figure 5:
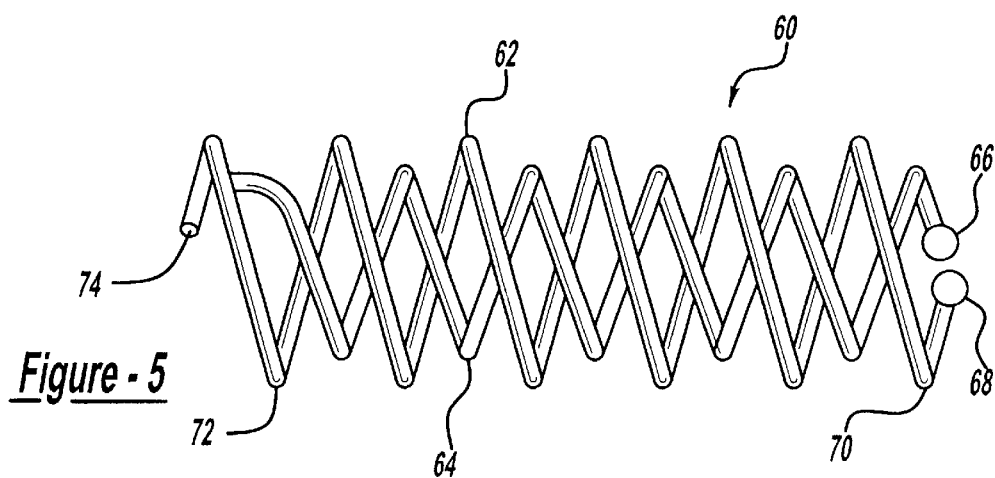
FIG. 5 is a side view of an intravascular stent according to a third preferred embodiment of the present invention.

Referring now to FIG. 5, a double helix stent according to another embodiment of the present invention is shown generally at 60. The counter helix stent 60 includes two individual lengths of resilient wire 62 and 64, having the same qualities as the stent 10. The wires 62 and 64 may have identical or differing diameters, according to specific design parameters. Alternatively, the stent 60 may be formed in a double helix configuration through use of a single length of wire or coil formed on a properly designed mandrel (not shown) having both right and left hand threads, by heat-treating a single length of resilient material to give the material a double helical configuration similar to that shown in FIG. 5. Of course, a similar construction may be obtained by joining or welding the proximal or distal ends of the wires 62 and 64 of counter-helical stent 60.

The first resilient wire 62 is wound in a right-hand threaded direction, while the second resilient wire 64 is wound in a left-hand threaded direction. Each wire thus provides support for the other to resist collapse of the stent 60 in both radial and axial directions, upon the application of external forces. The stent 60 may preferably include two distal beads 66 and 68 at its distal end 70, to be atraumatic to the vessel. In addition, both tips of the proximal end 72 may preferably be joined together at 74 to provide a point at which the stent can be advanced through a microcatheter using a pusher or a detachable pusher mechanism, such as that shown at 18 in FIG. 3.

Figure 6:
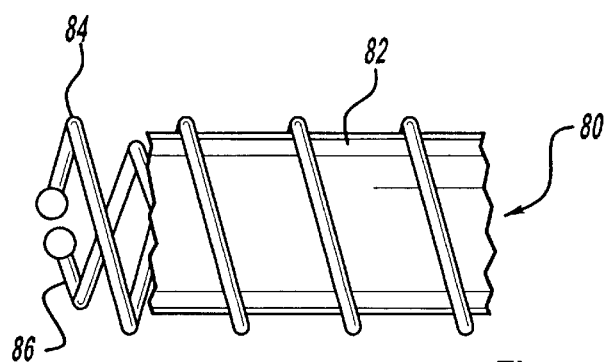
FIG. 6 is a side view of an intravascular stent according to a fourth preferred embodiment of the present invention.

Referring now to FIG. 6, a stent system according to another preferred embodiment of the present invention is shown generally at 80, in which the stent is further provided with a sleeve, covering or sheath. Such a sleeve is intended to more effectively treat and seal a particular vascular defect. The stent 80 may be of a counter helix configuration similar to that of stent 60 shown in FIG. 5. Stent 80 in FIG. 6 also includes elastic sleeve 82 within the two stents 84 and 86. The sleeve 82 may provide additional stent support for better occlusion of the neck 43 of aneurysm 44 shown in FIG. 4. Preferably, the sleeve 82 is attached between the two stents 84 and 86, in other words, inside stent 84 and outside stent 86. Thus, the stent system can still be collapsed to a substantially linear configuration when inserted into a catheter during placement and deployment of the stent. Alternatively, the sleeve 82 may be attached within, or outside, both stents 84 and 86.

Figure 7:
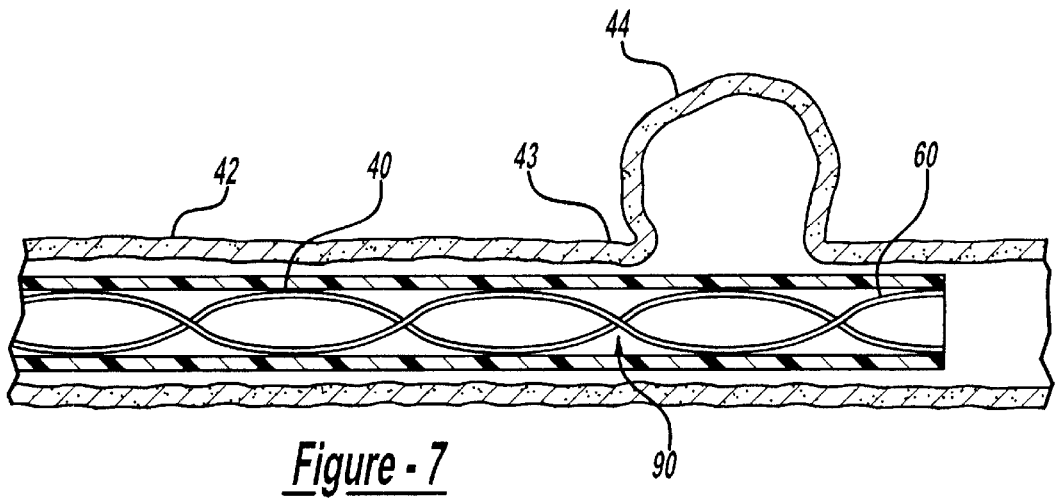
FIGS. 7 through 10 illustrate a preferred method of deployment of a stent according to the present invention.
Figure 8:
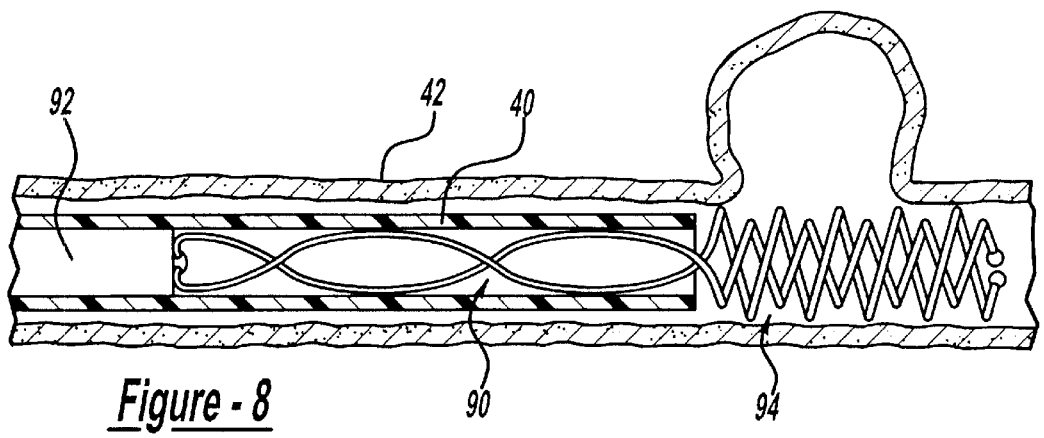

FIGS. 7–10 illustrate the deployment of the stent of the present invention, with particular reference to the counter-helix stent 60 in FIG. 5. However, it should be understood that delivery and deployment of stents according to all of the preferred embodiments of the present invention are similar. Referring first to FIG. 7, the stent 60 is inserted into the microcatheter 40, and assumes a substantially deformed or stretched linear configuration as shown generally at 90. The microcatheter is then moved into close proximity to the vascular defect, in this case the neck 43 of an aneurysm 44. After being placed near the aneurysm 44, the stent 60 is pushed out of the distal end of the microcatheter by the pusher 92, and the microcatheter is withdrawn slightly in the proximal direction, as shown at 94 in FIG. 8. The stent 60 resiliently assumes its relaxed counter-helix configuration as shown at 94, while the portion of the stent 60 remaining within the microcatheter is held in a generally linear configuration as shown at 90.

Figure 9:
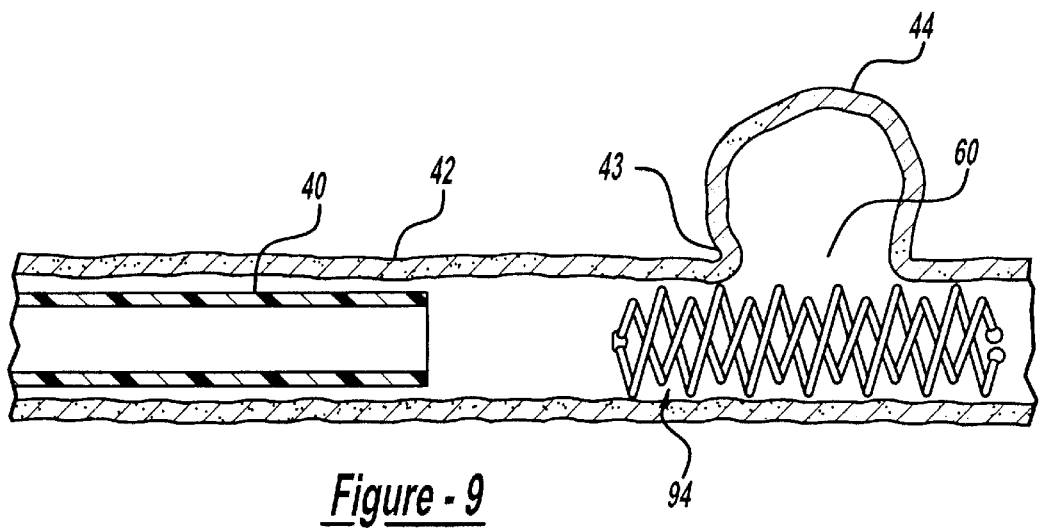

Referring to FIG. 9, once the stent is completely pushed out of the microcatheter 40, the entire stent reassumes its relaxed helical configuration. The stent 60 in its relaxed configuration has an associated diameter that tends to be somewhat greater than the diameter of the vessel 42, causing the stent 60 to gently press outward against the wall of the vessel 42. Therefore, the stent 60 tends to hold itself in place at the desired location across the vascular defect, such as the aneurysm 44.

Figure 10:
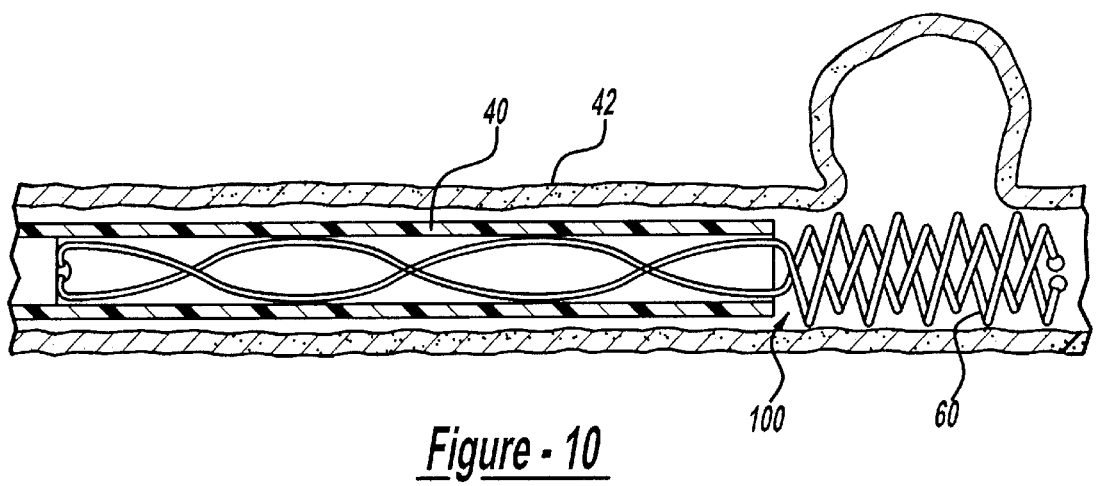

However, as shown in FIG. 10, if it is determined that the stent has been incorrectly positioned, the stent may be withdrawn back into the catheter, as indicated at 100, thus becoming stretched again to a substantially linear configuration with an associated smaller diameter. Once the stent has been withdrawn into the microcatheter, the microcatheter may be repositioned within the blood vessel to thereby effectively reposition the stent properly in the desired position.

Figure 11:
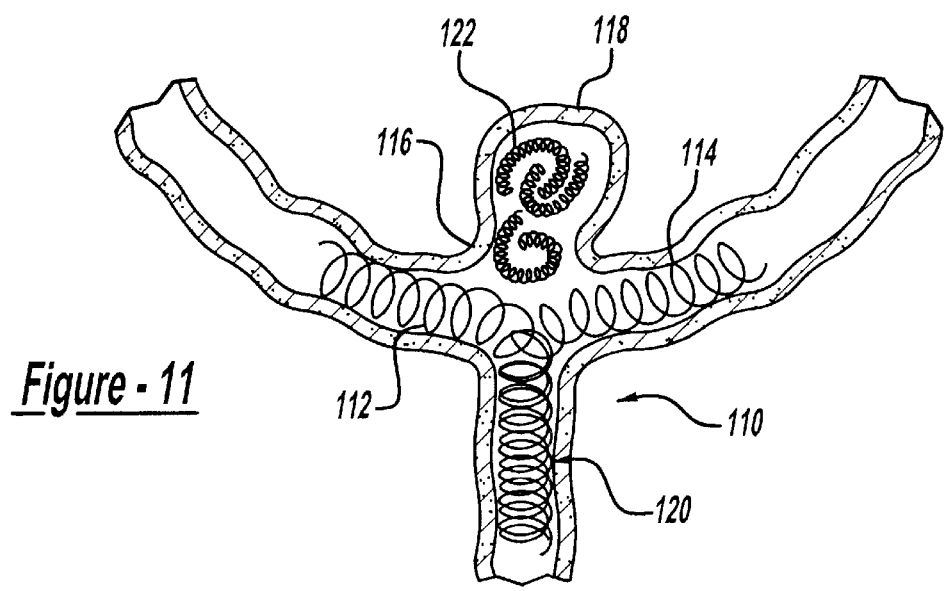
FIG. 11 is a side view of an intravascular stent system and embolic coil according to a fifth preferred embodiment of the present invention.

As depicted in FIG. 11, a vascular defect such as aneurysm 118 may develop at a location where one vessel branches off from another, referred to as a vessel "bifurcation," such as that shown generally at 116. A stent system for treating this type of vascular defect near a bifurcation is shown generally at 110, according to another preferred embodiment of the present invention.

The stent system 110 consists essentially of two individual wire stents 112 and 114, each being similar in structure and function to the stent 10 shown in FIG. 1. Wire stents 112 and 114 may be arranged in parallel helixes as shown in FIG. 11, or more preferably wound in opposite directions in a counter-helix similar to that shown in FIGS. 5–10. The stents 112 and 114 are delivered serially through a microcatheter to treat aneurysm 118.

The stent 114 is placed in interlocking contact across the stent 112, with the proximal portions of stents 112 and 114 joining generally at 120. The stent helical windings interlock in a parallel or counter helix configuration before the vessel bifurcation, similar in structure to that of the counter helix stent 60 shown in FIG. 5. The stent system 110 thereby forms the desired lumens, and adds structural integrity to the vessels at the bifurcation aneurysm, that would not otherwise be possible with a single stent.

Moreover, it is desirable to fill the bifurcation aneurysm 118 with embolic agents, such as embolic coils 122, to embolize the aneurysm and reduce the pressure inside. Only a few embolic coils 122 are illustrated in FIG. 11 for the sake of clarity, though the aneurysm would preferably be filled with a sufficient number of embolic coils 122 to successfully embolize the aneurysm. Depending on the particular anatomy of a patient, the number of embolic coils 122 that might be required may vary from one to many.

It is also important to prevent the embolic agent or coils from escaping the aneurysm, which might cause embolization in an undesirable location. The stent system 110 of the present invention forms a shelf near the neck 116 of the bifurcation aneurysm 118, on which the embolic devices can rest. This important feature of the present invention thus enables the successful treatment of a bifurcation aneurysm.

From the foregoing description, it should be appreciated that according to the preferred embodiments of the present invention the stent is collapsible to a compressed, substantially linear configuration for delivery and deployment in a tissue vessel. The positioning and deployment of the stent of the present invention thereby may be performed with a lower level of associated trauma to the vessel, and can be realized in vessels having a significantly smaller diameter than has been possible before with conventional stents. The stent of the present invention may be configured in a counter helix configuration, a configuration having a mesh cover, or in a bifurcated configuration to adapt the stent to particular application needs, while maintaining the collapsibility and deployability characteristics associated with the resilient material from which it is configured.

It should be understood that an unlimited number of configurations for the present invention can be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A vascular stent system for treating a blood vessel defect near a position where a first and second blood vessel branch off from a parent vessel comprising:

a first stent formed of a wire having a proximal end and a distal end, said first stent being constructed from a resilient material which upon being stretched takes the form of a generally elongated helical shape having a large pitch and upon being released returns to a generally helical shape having a small pitch;

a second stent formed of a wire having a proximal end and a distal end, said second stent being constructed from a resilient material which upon being stretched takes the form of a generally elongated helical shape having a large pitch and upon being released returns to a generally helical shape having a small pitch;

a catheter having a proximal end, a distal end and a lumen therethrough;

said first and second stents being disposed within the lumen of said catheter and said first and second stents being interlocked and interwound, wherein upon deployment the first and second stents separate from each other if unconstrained, but remain interlocked and interwound if constrained within a single vessel.

2. The vascular stent system as defined in claim 1, wherein said first and second stents are joined at one end.

3. The vascular stent system as defined in claim 2, wherein said first and second stents are formed from a nickel titanium alloy.

4. The vascular stent system as defined in claim 3, wherein said first and second stents are comprised of radiopaque material.

5. The vascular stent system as defined in claim 4, wherein said first and second stents form counter helixes.

* * * * *